(12) United States Patent
Huang et al.

(10) Patent No.: US 11,666,629 B2
(45) Date of Patent: Jun. 6, 2023

(54) PEPTIDE INTERACTING WITH TOLL-LIKE RECEPTOR 2 AND THE COMPOSITION COMPRISING THE SAME

(71) Applicant: NATIONAL TAIPEI UNIVERSITY OF TECHNOLOGY, Taipei (TW)

(72) Inventors: Chih-Hung Huang, Taipei (TW); Pu-Chieh Chang, Taipei (TW)

(73) Assignee: NATIONAL TAIPEI UNIVERSITY OF TECHNOLOGY, Taipei (TW)

( * ) Notice: Subject to any disclaimer, the term of this patent is extended or adjusted under 35 U.S.C. 154(b) by 71 days.

(21) Appl. No.: 17/144,609

(22) Filed: Jan. 8, 2021

(65) Prior Publication Data

US 2021/0213097 A1 Jul. 15, 2021

Related U.S. Application Data

(60) Provisional application No. 62/959,519, filed on Jan. 10, 2020.

(51) Int. Cl.
*A61K 38/16* (2006.01)
*A61P 3/04* (2006.01)
*A61K 39/39* (2006.01)

(52) U.S. Cl.
CPC ............ *A61K 38/164* (2013.01); *A61K 39/39* (2013.01); *A61P 3/04* (2018.01)

(58) Field of Classification Search
CPC .......... A61K 38/164; A61K 39/39; A61P 3/04
See application file for complete search history.

(56) References Cited

U.S. PATENT DOCUMENTS

2018/0265554 A1* 9/2018 Belzer ...................... C12N 1/20

OTHER PUBLICATIONS

Amuc_1100 family pilus-like protein [Akkermansia muciniphila], from https://www.ncbi.nlm.nih.gov/protein/WP_031930752.1?report=genbank&log$=prottop&blast_rank=1&RID=E53SUZCB016, pp. 1-2, accessed Jul. 28, 2022.*
Water, from http://www.biology-online.org/dictionary/Water, pp. 1-3, accessed Apr. 24, 2014.*
Myneni et al, Identification of a unique TLR2-interacting peptide motif in a microbial leucine-rich repeat protein, Biochemical and Biophysical Research Communications, 2012, 423, pp. 577-582.*

* cited by examiner

*Primary Examiner* — Li N Komatsu
(74) *Attorney, Agent, or Firm* — Birch, Stewart, Kolasch & Birch, LLP (57) ABSTRACT

Disclosed herein are peptide fragments of Amuc_1100* and the use thereof. The peptide is shown to be a ligand to activate TLR2 and is used to treat obesity and the related disease or condition. The peptide of the present invention is further used in the treatment of intestinal cancer, promoting immune response, and intestinal epithelial barrier dysfunction.

10 Claims, 7 Drawing Sheets

Specification includes a Sequence Listing.

SEQUENCE LISTING

```
<160> NUMBER OF SEQ ID NOS: 20

<210> SEQ ID NO 1
<211> LENGTH: 287
<212> TYPE: PRT
<213> ORGANISM: Akkermansia muciniphila

<400> SEQUENCE: 1

Ile Val Asn Ser Lys Arg Ser Glu Leu Asp Lys Ile Ser Ile Ala
1               5                   10                  15

Ala Lys Glu Ile Lys Ser Ala Asn Ala Ala Glu Ile Thr Pro Ser Arg
                20                  25                  30

Ser Ser Asn Glu Glu Leu Glu Lys Glu Leu Asn Arg Tyr Ala Lys Ala
            35                  40                  45

Val Gly Ser Leu Glu Thr Ala Tyr Lys Pro Phe Leu Ala Ser Ser Ala
    50                  55                  60

Leu Val Pro Thr Thr Pro Thr Ala Phe Gln Asn Glu Leu Lys Thr Phe
65                  70                  75                  80

Arg Asp Ser Leu Ile Ser Ser Cys Lys Lys Lys Asn Ile Leu Ile Thr
                85                  90                  95

Asp Thr Ser Ser Trp Leu Gly Phe Gln Val Tyr Ser Thr Gln Ala Pro
            100                 105                 110

Ser Val Gln Ala Ala Ser Thr Leu Gly Phe Glu Leu Lys Ala Ile Asn
        115                 120                 125

Ser Leu Val Asn Lys Leu Ala Glu Cys Gly Leu Ser Lys Phe Ile Lys
    130                 135                 140

Val Tyr Arg Pro Gln Leu Pro Ile Glu Thr Pro Ala Asn Asn Pro Glu
145                 150                 155                 160

Glu Ser Asp Glu Ala Asp Gln Ala Pro Trp Thr Pro Met Pro Leu Glu
                165                 170                 175

Ile Ala Phe Gln Gly Asp Arg Glu Ser Val Leu Lys Ala Met Asn Ala
            180                 185                 190

Ile Thr Gly Met Gln Asp Tyr Leu Phe Thr Val Asn Ser Ile Arg Ile
        195                 200                 205

Arg Asn Glu Arg Met Met Pro Pro Ile Ala Asn Pro Ala Ala Ala
    210                 215                 220

Lys Pro Ala Ala Ala Gln Pro Ala Thr Gly Ala Ala Ser Leu Thr Pro
225                 230                 235                 240

Ala Asp Glu Ala Ala Ala Pro Ala Ala Pro Ala Ile Gln Gln Val Ile
                245                 250                 255

Lys Pro Tyr Met Gly Lys Glu Gln Val Phe Val Gln Val Ser Leu Asn
            260                 265                 270

Leu Val His Phe Asn Gln Pro Lys Ala Gln Glu Pro Ser Glu Asp
        275                 280                 285

<210> SEQ ID NO 2
<211> LENGTH: 32
```

```
<212> TYPE: PRT
<213> ORGANISM: Akkermansia muciniphila

<400> SEQUENCE: 2

Ile Val Asn Ser Lys Arg Ser Glu Leu Asp Lys Lys Ile Ser Ile Ala
1               5                   10                  15

Ala Lys Glu Ile Lys Ser Ala Asn Ala Ala Glu Ile Thr Pro Ser Arg
            20                  25                  30

<210> SEQ ID NO 3
<211> LENGTH: 32
<212> TYPE: PRT
<213> ORGANISM: Akkermansia muciniphila

<400> SEQUENCE: 3

Ser Ser Asn Glu Glu Leu Glu Lys Glu Leu Asn Arg Tyr Ala Lys Ala
1               5                   10                  15

Val Gly Ser Leu Glu Thr Ala Tyr Lys Pro Phe Leu Ala Ser Ser Ala
            20                  25                  30

<210> SEQ ID NO 4
<211> LENGTH: 27
<212> TYPE: PRT
<213> ORGANISM: Akkermansia muciniphila

<400> SEQUENCE: 4

Leu Val Pro Thr Thr Pro Thr Ala Phe Gln Asn Glu Leu Lys Thr Phe
1               5                   10                  15

Arg Asp Ser Leu Ile Ser Ser Cys Lys Lys Lys
            20                  25

<210> SEQ ID NO 5
<211> LENGTH: 34
<212> TYPE: PRT
<213> ORGANISM: Akkermansia muciniphila

<400> SEQUENCE: 5

Asn Ile Leu Ile Thr Asp Thr Ser Ser Trp Leu Gly Phe Gln Val Tyr
1               5                   10                  15

Ser Thr Gln Ala Pro Ser Val Gln Ala Ala Ser Thr Leu Gly Phe Glu
            20                  25                  30

Leu Lys

<210> SEQ ID NO 6
<211> LENGTH: 16
<212> TYPE: PRT
<213> ORGANISM: Akkermansia muciniphila

<400> SEQUENCE: 6

Asn Ile Leu Ile Thr Asp Thr Ser Ser Trp Leu Gly Phe Gln Val Tyr
1               5                   10                  15

<210> SEQ ID NO 7
<211> LENGTH: 18
<212> TYPE: PRT
<213> ORGANISM: Akkermansia muciniphila

<400> SEQUENCE: 7

Ser Thr Gln Ala Pro Ser Val Gln Ala Ala Ser Thr Leu Gly Phe Glu
1               5                   10                  15

Leu Lys
```

<210> SEQ ID NO 8
<211> LENGTH: 25
<212> TYPE: PRT
<213> ORGANISM: Akkermansia muciniphila

<400> SEQUENCE: 8

Ala Ile Asn Ser Leu Val Asn Lys Leu Ala Glu Cys Gly Leu Ser Lys
1               5                   10                  15

Phe Ile Lys Val Tyr Arg Pro Gln Leu
            20                  25

<210> SEQ ID NO 9
<211> LENGTH: 12
<212> TYPE: PRT
<213> ORGANISM: Akkermansia muciniphila

<400> SEQUENCE: 9

Ala Ile Asn Ser Leu Val Asn Lys Leu Ala Glu Cys
1               5                   10

<210> SEQ ID NO 10
<211> LENGTH: 13
<212> TYPE: PRT
<213> ORGANISM: Akkermansia muciniphila

<400> SEQUENCE: 10

Gly Leu Ser Lys Phe Ile Lys Val Tyr Arg Pro Gln Leu
1               5                   10

<210> SEQ ID NO 11
<211> LENGTH: 24
<212> TYPE: PRT
<213> ORGANISM: Akkermansia muciniphila

<400> SEQUENCE: 11

Pro Ile Glu Thr Pro Ala Asn Asn Pro Glu Glu Ser Asp Glu Ala Asp
1               5                   10                  15

Gln Ala Pro Trp Thr Pro Met Pro
            20

<210> SEQ ID NO 12
<211> LENGTH: 27
<212> TYPE: PRT
<213> ORGANISM: Akkermansia muciniphila

<400> SEQUENCE: 12

Leu Glu Ile Ala Phe Gln Gly Asp Arg Glu Ser Val Leu Lys Ala Met
1               5                   10                  15

Asn Ala Ile Thr Gly Met Gln Asp Tyr Leu Phe
            20                  25

<210> SEQ ID NO 13
<211> LENGTH: 14
<212> TYPE: PRT
<213> ORGANISM: Akkermansia muciniphila

<400> SEQUENCE: 13

Leu Glu Ile Ala Phe Gln Gly Asp Arg Glu Ser Val Leu Lys
1               5                   10

<210> SEQ ID NO 14
<211> LENGTH: 13
<212> TYPE: PRT

```
<213> ORGANISM: Akkermansia muciniphila

<400> SEQUENCE: 14

Ala Met Asn Ala Ile Thr Gly Met Gln Asp Tyr Leu Phe
1               5                   10

<210> SEQ ID NO 15
<211> LENGTH: 11
<212> TYPE: PRT
<213> ORGANISM: Akkermansia muciniphila

<400> SEQUENCE: 15

Thr Val Asn Ser Ile Arg Ile Arg Asn Glu Arg
1               5                   10

<210> SEQ ID NO 16
<211> LENGTH: 26
<212> TYPE: PRT
<213> ORGANISM: Akkermansia muciniphila

<400> SEQUENCE: 16

Met Met Pro Pro Pro Ile Ala Asn Pro Ala Ala Lys Pro Ala Ala
1               5                   10                  15

Ala Gln Pro Ala Thr Gly Ala Ala Ser Leu
            20                  25

<210> SEQ ID NO 17
<211> LENGTH: 24
<212> TYPE: PRT
<213> ORGANISM: Akkermansia muciniphila

<400> SEQUENCE: 17

Thr Pro Ala Asp Glu Ala Ala Pro Ala Ala Pro Ala Ile Gln Gln
1               5                   10                  15

Val Ile Lys Pro Tyr Met Gly Lys
            20

<210> SEQ ID NO 18
<211> LENGTH: 25
<212> TYPE: PRT
<213> ORGANISM: Akkermansia muciniphila

<400> SEQUENCE: 18

Glu Gln Val Phe Val Gln Val Ser Leu Asn Leu Val His Phe Asn Gln
1               5                   10                  15

Pro Lys Ala Gln Glu Pro Ser Glu Asp
            20                  25

<210> SEQ ID NO 19
<211> LENGTH: 11
<212> TYPE: PRT
<213> ORGANISM: Akkermansia muciniphila

<400> SEQUENCE: 19

Glu Gln Val Phe Val Gln Val Ser Leu Asn Leu
1               5                   10
```

```
<210> SEQ ID NO 20
<211> LENGTH: 14
<212> TYPE: PRT
<213> ORGANISM: Akkermansia muciniphila

<400> SEQUENCE: 20

Val His Phe Asn Gln Pro Lys Ala Gln Glu Pro Ser Glu Asp
1               5                   10
```

PEPTIDE INTERACTING WITH TOLL-LIKE RECEPTOR 2 AND THE COMPOSITION COMPRISING THE SAME

CROSS REFERENCE

This Non-provisional application claims the priority under 35 U.S.C. § 119(a) on U.S. Patent Provisional Application No. 62/959,519 filed on Jan. 10, 2020, the entire contents of which are hereby incorporated by reference.

FIELD OF THE INVENTION

The present invention is directed to a peptide interacting with Toll-like receptor 2 (TLR2), and some peptides for treating obesity, their composition and use.

BACKGROUND OF THE INVENTION

Gut microbiome comprises approximately 100 trillion microbes residing and is correlated to the host's health condition. It is reported that the gut microbiome effects and mediates the metabolism, nutrition, and immunity response of the host. Thus, the microbe in the gut is a potential objective for diagnosis, prophylaxis, treatment, and prognosis.

*Akkermansia* spp. is a family of bacteria isolated from the human intestinal flora. *Akkermansia muciniphila* has been previously reported to be reduced in fecal samples from obese individuals and patients with inflammatory bowel disease. In particular, the protein Amuc_1100, a specific protein isolated from the outer membrane of *A. muciniphila*, is considered to be the active agent in the treatment of obesity and is therefore a potential medicament. As Amuc_1100 interacts with Toll-like receptor 2, it improves the gut barrier and partly recapitulates the beneficial effects of the bacterium.

However, it is reported that the pharmaceutically active protein of *Akkermansia muciniphila* is stable at a temperature used for pasteurization, but would be denatured and ineffective after autoclavation. It is desirable to find or develop new peptides which can be autoclaved but still retains the activity.

SUMMARY OF THE INVENTION

Accordingly, the present invention provides some new peptides that interacts with Toll-like receptor 2 (TLR2).

An aspect provided herein is a synthetic peptide interacting with TLR2, comprising an amino acid sequence consisting of SEQ ID NO: 8, but having a length up to 50 amino acids.

In one embodiment, the synthetic peptide has a length up to 30 amino acids.

In one embodiment, the synthetic peptide consists of the amino acid sequence of SEQ ID NO: 8.

Another aspect provided herein is a composition for the treatment of TLR2-related disease comprising a pharmaceutically acceptable carrier, and at least one peptide comprising one fragment set forth in SEQ ID NO: 8.

Another aspect provided herein is a method of treatment of TLR2-related disease, comprising administering to a subject in need a therapeutically effective amount of a synthetic peptide comprising an amino acid sequence consisting of SEQ ID NO: 8.

In one embodiment, the synthetic peptide is administered orally or parenterally.

Another aspect provided herein is a synthetic peptide having an efficacy in treating obesity, comprising an amino acid sequence selected from the group consisting those of SEQ ID NO: 10, SEQ ID NO: 15, SEQ ID NO: 19, and SEQ ID NO: 20, but having a length up to 50 amino acids.

In one embodiment, the synthetic peptide has a length up to 30 amino acids.

In one embodiment, the synthetic peptide consists of the amino acid sequence of SEQ ID NO: 10.

In one embodiment, the synthetic peptide consists of the amino acid sequence of SEQ ID NO: 8.

In one embodiment, the synthetic peptide consists of the amino acid sequence of SEQ ID NO: 15.

In one embodiment, the synthetic peptide consists of the amino acid sequence of SEQ ID NO: 19.

In one embodiment, the synthetic peptide consists of the amino acid sequence of SEQ ID NO: 20.

Another aspect provided herein is a pharmaceutical composition for the treatment of obesity comprising a pharmaceutically acceptable carrier, and at least one peptide comprising one fragment selected from the group consisting of those set forth in SEQ ID NO: 10, SEQ ID NO: 15, SEQ ID NO: 19, and SEQ ID NO: 20.

Another aspect provided herein is a method for the treatment of obesity, comprising administering to a subject in need a therapeutically effective amount of a synthetic peptide comprising an amino acid sequence consisting of SEQ ID NO: 10, SEQ ID NO: 15, SEQ ID NO: 19, and SEQ ID NO: 20.

In one embodiment, the synthetic peptide is administered orally or parenterally.

In one embodiment, the synthetic peptide provides an efficacy in promoting immune response.

In one embodiment, the peptide is co-administered with a vaccine and is used as an adjuvant.

Another aspect provided herein is a method of preventing intestinal cancer and reducing intestinal carcinogen toxicity comprising administering to a subject in need a therapeutically effective amount of an isolated peptide comprising the peptide as disclosed herein.

In one embodiment, the synthetic peptide is administered orally or parenterally.

Another aspect provided herein is a method of treatment of a disease caused by intestinal epithelial barrier dysfunction comprising administering to a subject in need a therapeutically effective amount of the peptide as disclosed herein.

In one embodiment, the disease caused by intestinal epithelial barrier dysfunction is inflammatory bowel disease, celiac disease, diarrhoeal diseases, type II diabetes, obesity, or non-alcoholic fatty liver disease (NAFLD).

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings:

FIG. 1 shows the induction of TLR2 in recombinant HEK-293 with the peptide as disclosed herein: (A) recombinant HEK-293 functionally overexpressing human TLR and a reporter gene (SEAP); (B): HEK-293 null as negative control. Only AMS5 shows the activity for induction of TLR whereas other peptides do not. PC: positive control; NC: negative control; GST: glutathione S-transferase (null)

DESCRIPTION OF THE INVENTION

The following embodiments when read with the accompanying drawings are made to clearly exhibit the above-mentioned and other technical contents, features and effects of the present disclosure. As the contents disclosed herein should be readily understood and can be implemented by a person skilled in the art, all equivalent changes or modifications which do not depart from the concept of the present disclosure should be encompassed by the appended claims.

Unless otherwise stated, the following terms used in this application, including the specification and claims, have the definitions given below.

As used in the specification and the appended claims, the singular forms "a," "an" and "the" include plural referents unless the context clearly dictates otherwise. Unless otherwise indicated, conventional methods of protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

The term "amino acid" used herein is used in its broadest sense and is meant to include, but is not limited to, the naturally-occurring L-amino acids or residues.

The terms "polypeptide," "peptide," and "protein," used interchangeably herein, refer to a polymeric form of amino acids of any length, which can include naturally-occurring amino acids, coded and non-coded amino acids, chemically or biochemically modified, derivatized, or designer amino acids, amino acid analogs, peptidomimetics, and depsipeptides, and polypeptides having modified, cyclic, bicyclic, depsicyclic, or depsibicyclic peptide backbones. The term includes single chain protein as well as multimers.

The term "ligand" refers to a molecule that binds to another molecule, including a receptor.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a peptide or protein as disclosed herein required to provide a clinically significant decrease in disease symptoms. An appropriate "effective" amount in any individual case may be determined using techniques, such as a dose escalation study.

The term "composition" as used herein, refers a product that results from the mixing or combining of more than one active ingredient and includes both fixed and non-fixed combinations of the active ingredients. The term "fixed combination" means that the active ingredients and a certain co-agent are both administered to a patient simultaneously in the form of a single entity or dosage. The term "non-fixed combination" means that the active ingredients and a certain co-agent are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "composition" as used herein also refers to a mixture that usually contains a pharmaceutically acceptable carrier, such as a pharmaceutically acceptable carrier or excipient that is conventional in the art.

The terms "co-administration" or the like, as used herein, are meant to encompass administration of the selected therapeutic agents to a single patient, and are intended to include treatment regimens in which the agents are administered by the same or different route of administration sequentially or simultaneously.

The term "carrier," as used herein, refers to relatively nontoxic chemical compounds or agents that facilitate the incorporation of a compound into cells or tissues.

The pharmaceutically acceptable carrier(s) can be selected from, for example, excipients, adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions.

Examples of suitable excipient include but are not limited to lactose, glucose, sucrose, sorbitol, mannose, starch, arabia gum, calcium phosphate, alginate, tragacanth gum, gelatin, calcium silicate, microcrystalline cellulose, polyvinylpyrrolidone (PVP), cellulose, ddH$_2$O, syrup, or methylcellulose.

A "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "disease" used herein refers to any condition, infection, disorder, or syndrome that requires medical intervention or for which medical intervention is desirable. Such medical intervention can include treatment, diagnosis, and/or prevention.

*Akkermansia muciniphila* is a species of human intestinal mucin-degrading bacterium, which was firstly found in 2004. *A. muciniphila* is a Gram-negative, strictly anaerobic, non-motile, non-spore-forming, oval-shaped bacterium. *A. muciniphila* is believed to have anti-inflammatory effects in humans, and studies have shown inverse relationships between *A. muciniphila* colonization and inflammatory conditions such as appendicitis or inflammatory bowel disease (IBD).

It is believed that the reduction of *A. muciniphila* in human gut is highly correlated to certain pathological condition and thus *A. muciniphila* is a beneficial microbe for its potential use as medicament or nutrition food.

Amuc_1100* is an outer membrane protein of *Akkermansia*, which has been identified and is found to activate intracellular signals mediated by the Toll-like receptor 2 (TLR2) of intestinal epithelial cells, contributing to the enhancement of the intestinal barrier. It has been disclosed that Amuc_1100* is involved in the immune response, specifically in the induction of the production of interleukin-10 (IL-10), which is an anti-inflammatory cytokine.

Toll-like receptors (TLRs) are the transmembrane proteins which includes 13 classes and are expressed in a wide spectrum of cells and tissues including immunocompetent cells such as macrophages and neutrophils, vascular endothelial cells, and renal intrinsic cells such as renal tubular epithelial cells. Activation of TLR induces the expression of inflammatory cytokines such as tumor necrosis factor-alpha (TNF-α) and interleukin 6 (IL-6) and elicits an inflammatory response, for example, through the activation of a nuclear factor-kappa B (NF-κB) which is a transcription factor. Such TLR-mediated activation of various cells is known to be involved in immune inflammatory diseases such as sepsis, acute renal failure, chronic renal disease, acute respiratory distress syndrome, scleroderma, acute pancreatitis, and chronic obstructive pulmonary disease.

Toll-like receptor 2, also known as "TLR2," refers to a protein that in humans is encoded by the TLR2 gene. TLR2 has also been designated as "CD282" (cluster of differentiation 282). TLR2 is one of the toll-like receptors and plays a role in the immune system. TLR2 is a membrane protein, a receptor, which is expressed on the surface of certain cells and recognizes foreign substances and passes on appropriate signals to the cells of the immune system. In the intestine, TLR2 regulates the expression of CYP1 A1, which is a key enzyme in detoxication of carcinogenic polycyclic aromatic hydrocarbons such as hydrocarbons such as hezo(a)pyrene, The term "TLR2-related disease", "condition or disorder associated with TLR2", or the like used herein refers to any disease state associated with a toll-like receptor 2. Such diseases or disorders include, but are not limited to, infectious diseases, inflammatory diseases, respiratory diseases, immunity diseases, and gastrointestinal and colorectal disease.

In some embodiment of the present disclosure, the TLR2-related disease is intestinal epithelial barrier dysfunction, such as inflammatory bowel disease, celiac disease, diarrhoeal diseases, type II diabetes, obesity, or non-alcoholic fatty liver disease (NAFLD). Accordingly, as the dysfunction of intestinal epithelial barrier is mitigated, the carcinogen adsorb by the intestine is reduced, and further intestinal carcinogen toxicity is reduced and intestinal cancer is prevented. Still further, as the intestinal epithelial barrier is malfunctioned, the TLR2-related disease is further associated to obesity. Accordingly, the TLR2-related disease includes obesity.

The term "obesity" used herein refers to an excessive accumulation of body fat in the body.

The term "immune response" or "immunological response" to an antigen or composition used herein refers to the development in a subject of a humoral and/or cellular immune response to the antigen or composition.

According to the present invention, the composition or pharmaceutical composition comprising the peptide can be prepared in any form suitable for oral, parenteral, topical, intranasal, intrabronchial, sublingual, rectal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical dosage forms suitable for oral administration include tablets, capsules (hard or soft shell), caplets, pills, lozenges, syrups, solutions, powders, granules, elixirs, suspensions, sublingual tablets, wafers, or patches such as buccal patches.

For oral administration, fine powders or granules may contain diluting, dispersing, and/or surface active agents, and may be presented in water or in a syrup, in capsules or sachets in the dry state, or in a non-aqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

The pharmaceutical composition as disclosed herein can be preserved by lyophilization and can be reconstructed with a suitable carrier before use. The lyophilization and reconstruction can be performed according to the ordinary skills in the art and a skilled person would appreciate that lyophilization and reconstruction contribute to a certain degree of loss of activity and the dose of pharmaceutical should be adjusted upwards for compensation. The pharmaceutical composition as disclosed herein can also be manufactured by the process such as spray drying, drum drying, or vacuum drying, but is not limited hereto.

As defined herein, Amuc_1100 refers to the full length of protein Amuc_1100, which can be obtained from common databases; Amuc_1100* defined herein refers to the protein Amuc_1100 which does not include the transmembrane domain thereof and is presented herein as SEQ ID NO: 1.

According to the present invention some synthetic peptides are designed on the basis of some amino acid fragments derived from Amuc_1100. In particular, the synthetic peptide comprising an amino acid sequence selected from the group consisting of SEQ ID NO: 10, SEQ ID NO: 15, SEQ ID NO: 19, and SEQ ID NO: 20.

In some embodiment, the peptide has a length up to 50 amino acids. In some embodiment, the peptide has a length up to 40 amino acids. In some embodiment, the peptide has a length up to 30 amino acids. In some embodiment, the peptide has a length up to 20 amino acids.

In some embodiment, the peptides used herein are used as a ligand that elicits the downstream signal of Toll-like receptor (TLR), particularly TLR2.

An aspect provided herein is a synthetic peptide interacting with TLR2, comprising an amino acid sequence consisting of SEQ ID NO: 8; but having a length up to 50 amino acids.

In one embodiment, the synthetic peptide has a length up to 30 amino acids.

In one embodiment, the synthetic peptide consists of the amino acid sequence of SEQ ID NO: 8.

Another aspect provided herein is a composition for the treatment of TLR2-related disease comprising a pharmaceutically acceptable carrier, and at least one peptide comprising one fragment set forth in SEQ ID NO: 8.

Another aspect provided herein is a method of treatment of TLR2-related disease, comprising administering to a subject in need a therapeutically effective amount of a synthetic peptide comprising an amino acid sequence consisting of SEQ ID NO: 8.

In one embodiment, the synthetic peptide is administered orally or parenterally.

Another aspect provided herein is a synthetic peptide having an efficacy in treating obesity, comprising an amino acid sequence selected from the group consisting those of SEQ ID NO: 10, SEQ ID NO: 15, SEQ ID NO: 19, and SEQ ID NO: 20, but having a length up to 50 amino acids.

In one embodiment, the synthetic peptide has a length up to 30 amino acids.

In one embodiment, the synthetic peptide consists of the amino acid sequence of SEQ ID NO: 10.

In one embodiment, the synthetic peptide consists of the amino acid sequence of SEQ ID NO: 8.

In one embodiment, the synthetic peptide consists of the amino acid sequence of SEQ ID NO: 15.

In one embodiment, the synthetic peptide consists of the amino acid sequence of SEQ ID NO: 19.

In one embodiment, the synthetic peptide consists of the amino acid sequence of SEQ ID NO: 20.

Another aspect provided herein is a pharmaceutical composition for the treatment of obesity comprising a pharmaceutically acceptable carrier, and at least one peptide comprising one fragment selected from the group consisting of those set forth in SEQ ID NO: 10, SEQ ID NO: 15, SEQ ID NO: 19, and SEQ ID NO: 20.

Another aspect provided herein is a method for the treatment of obesity, comprising administering to a subject in need a therapeutically effective amount of a synthetic peptide comprising an amino acid sequence consisting of SEQ ID NO: 10, SEQ ID NO: 15, SEQ ID NO: 19, and SEQ ID NO: 20.

In one embodiment, the synthetic peptide is administered orally or parenterally.

In one embodiment, the synthetic peptide provides an efficacy in promoting immune response.

In one embodiment, the peptide is co-administered with a vaccine and is used as an adjuvant.

Another aspect provided herein is a method of preventing intestinal cancer and reducing intestinal carcinogen toxicity comprising administering to a subject in need a therapeutically effective amount of an isolated peptide comprising the peptide as disclosed herein.

In one embodiment, the synthetic peptide is administered orally or parenterally.

Another aspect provided herein is a method of treatment of a disease caused by intestinal epithelial barrier dysfunction comprising administering to a subject in need a therapeutically effective amount of the peptide as disclosed herein.

In one embodiment, the disease caused by intestinal epithelial barrier dysfunction is inflammatory bowel disease, celiac disease, diarrhoeal diseases, type II diabetes, obesity, or non-alcoholic fatty liver disease (NAFLD).

EXAMPLES

Example 1 Preparation of Lysis Peptides of Amuc_1100*

The full length of Amuc_1100* essentially comprises 317 amino acids, approximately 17,384 kDa (SEQ ID NO: 1).

Amuc_1100* can be also divided into fragments as shown in Table 1 below.

TABLE 1

| Name | SEQ ID Number | Sequence |
| --- | --- | --- |
| AMS1 | SEQ ID NO: 2 | IVNSKRSELDKKISIAAKEIKSANAAEITPSR |
| AMS2 | SEQ ID NO: 3 | SSNEELEKELNRYAKAVGSLETAYKPFLASSA |
| AMS3 | SEQ ID NO: 4 | LVPTTPTAFQNELKTFRDSLISSCKKK |
| AMS4 | SEQ ID NO: 5 | NILITDTSSWLGFQVYSTQAPSVQAASTLGFELK |
| AMS4-1 | SEQ ID NO: 6 | NILITDTSSWLGFQVY |
| AMS4-2 | SEQ ID NO: 7 | STQAPSVQAASTLGFELK |
| AMS 5 | SEQ ID NO: 8 | AINSLVNKLAECGLSKFIKVYRPQL |
| AMS5-1 | SEQ ID NO: 9 | AINSLVNKLAEC |
| AMS5-2 | SEQ ID NO: 10 | GLSKFIKVYRPQL |
| AMS6 | SEQ ID NO: 11 | PIETPANNPEESDEADQAPWTPMP |
| AMS7 | SEQ ID NO: 12 | LEIAFQGDRESVLKAMNAITGMQDYLF |
| AMS7-1 | SEQ ID NO: 13 | LEIAFQGDRESVLK |
| AMS7-2 | SEQ ID NO: 14 | AMNAITGMQDYLF |
| AMS8 | SEQ ID NO: 15 | TVNSIRIRNER |
| AMS9 | SEQ ID NO: 16 | MMPPPIANPAAAKPAAAQPATGAASL |
| AMS10 | SEQ ID NO: 17 | TPADEAAAPAAPAIQQVIKPYMGK |
| AMS11 | SEQ ID NO: 18 | EQVFVQVSLNLVHFNQPKAQEPSED |
| AMS11-1 | SEQ ID NO: 19 | EQVFVQVSLNL |
| AMS11-2 | SEQ ID NO: 20 | VHFNQPKAQEPSED |

The production and purification of the peptides set forth in Table 1 comprises the following steps.

The expression plasmids were originated from pET28a with fragments of Amuc_1100*. The fragments were cloned at the C terminal of glutathione S-transferase (GST) to form a fusion protein upon expression in *E. coli*. The bacterial culture was incubated in LB broth, followed by the induction by adding 1 mM IPTG in the growth medium during mid-exponential phase. After 3 hours of IPTG induction, the bacteria were pelleted by centrifuging and were stored at −20° C.

The bacteria were resuspended and lysed with lysozyme and by sonification. Supernatant was collected after centrifugation and the desired fragment of peptide was purified through metal affinity purification under native conditions using ABT's Glutathione Resin. After buffer exchange in 0.1×PBS using 10K snakeskin dialysis column, the eluted peptides were confirmed with BCA assay and the peptide samples were stored at −20° C.

Biorad's CHT™ Ceramic Hydroxyapatite beads were used to remove the endotoxin from the eluted peptide after purification. Endotoxin detection was conducted using LAL (Limulis Amebocyte Lysate) kit in order to confirm the removal of endotoxin. The endotoxin in all peptide samples were measured under 10 EU/mL.

Example 2

Human Embryonic Kidney Cells 293 (HEK-293) were treated with the peptide fragments as disclosed herein.

Samples and controls are tested in duplicate on recombinant HEK-293 cell lines. These cell lines functionally overexpress human TLR as well as a reporter gene which is a secreted alkaline phosphatase (SEAP). The production of this reporter gene is driven by a NF-κB inducible promoter. The level of activation is given as optical density values (OD).

Samples in 100 μg/ml were diluted to a final concentration of 10 μg/ml in the reaction volume. Sample and controls are tested in duplicated wells. BSA is used as negative control.

SEAP reporter is detected as OD value. OD value is subtracted by average non-induced (NI) value. The NI subtracted duplicates are averaged and presented in a histogram. The reagents and materials employed in the instant examples were provided by Invivogen.

Figure 1A:
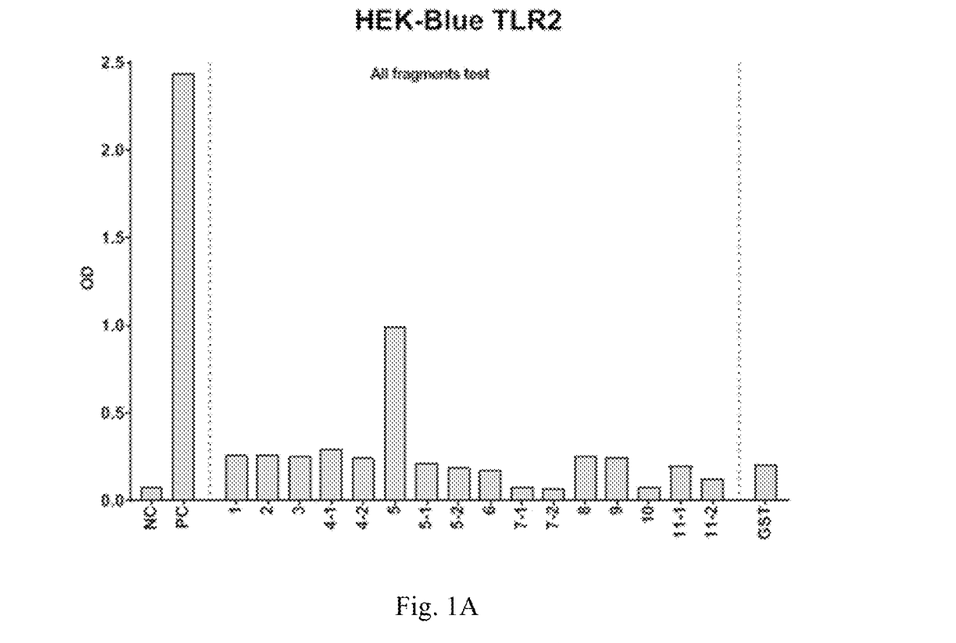
Figure 1B:
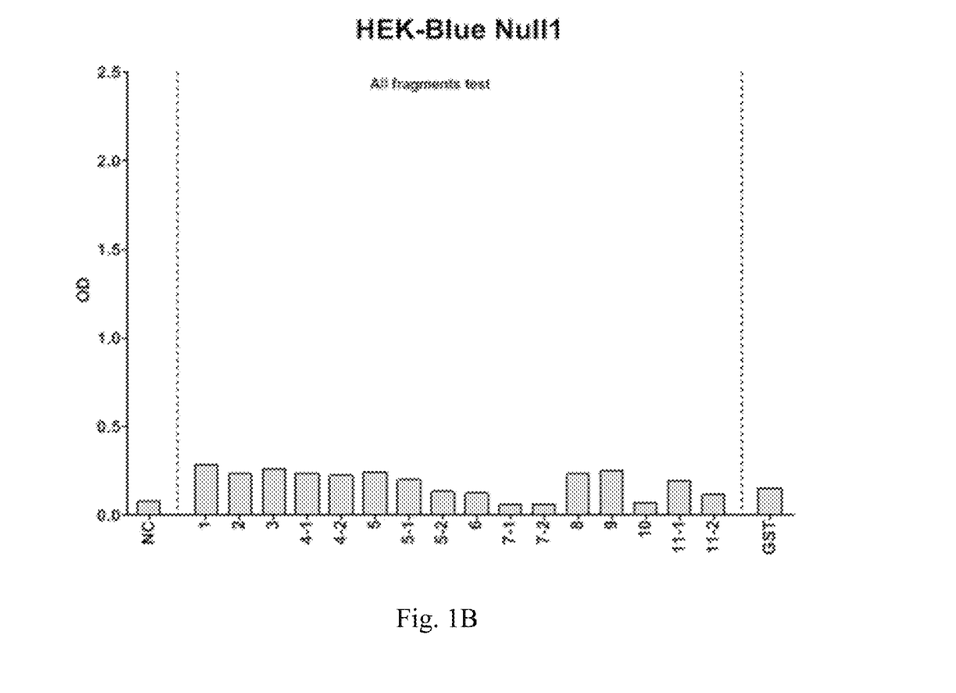

FIG. 1 shows the screening of the induction of TLRs by the peptides as disclosed herein. As shown in the FIG. 1A, human Toll-like receptor (TLR) was strongly and specifically activated in response to AMS5; whereas the null control shows that the HEK-293, whose TLR does not activate the reporter gene, does not respond to the treatment of any peptide as disclosed herein (FIG. 1B).

Accordingly, it can be concluded that AMS5 is capable to activate TLR2 whereas other fragments of Amuc_1100 do not. Hence AMS5 is a potential agent for TLR2-related diseases.

Example 3 Treatment of Obesity

Zebra fish has been for a long time used as a model of obesity in many reports (Hasumura et al. Nutrition & Metabolism (2012); Tainaka et al. Nutrition & Metabolism (2011); Oka et al. BMC Physiology (2010); Shimada et al. Nutrition & Metabolism (2015); Meguro et al. Scientific Reports (2019); Montalbano et al. Endocrine (2018); Yang et al. Cancer (2019)), which is also used herein as the subject of treatment of obesity with the peptides as disclosed herein.

All peptides used in the present example were purified through CHT beads to remove endotoxin. LAL assay was further conducted and it was confirmed that the residue of endotoxin was under 0.25 EU/ml.

Zebra fish was bred in 25° C. water (pH 6.5-7.5, conductivity 250-750 S·m$^{-1}$, NH$_3$<0.25 ppm, NO$_2$<0.25 ppm, NO$_3$<0.5 ppm) and was fed with normal diet bid. (brine shrimp). Each group of experimentation comprises 10 zebra fish (n=10).

The gavage feeding of Zebra fish follows the protocol disclosed in Collymore et al. (Journal of Visualized Experiment (2013)). During 13 days of experimentation, the zebra fish were fed once a day with the peptide fragments as disclosed herein in a 1× dose of 0.03 μg/day/fish. The weight of zebra fish was measured respectively on day 0, 1, 3, 6, 9, 12 and 13. In the present example, five groups of zebra fish were administered with the peptides as disclosed herein:
   Group 1: AMS4-1+AMS4-2
   Group 2: GST (null)
   Group 3: AMS1+AMS2
   Group 4: AMS3+AMS9
   Group 5: AMS5

Figure 2:
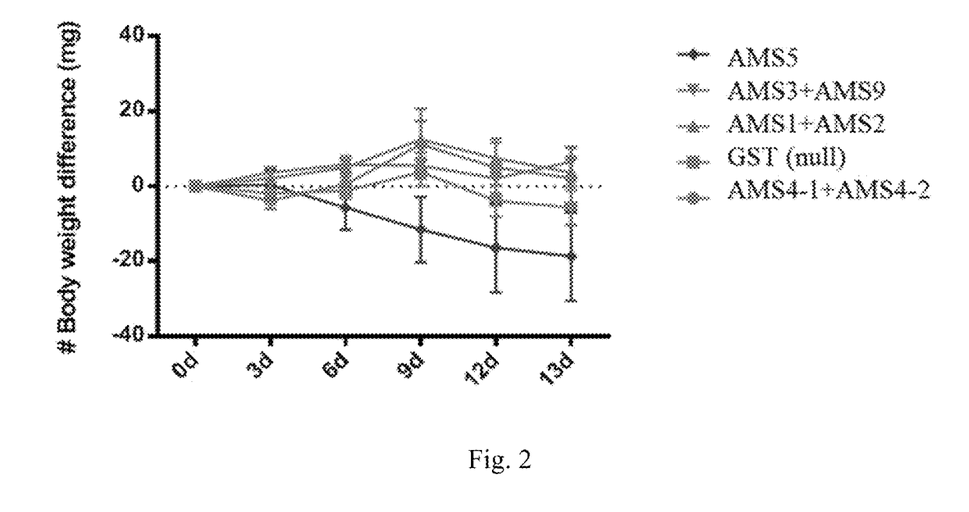
FIG. 2 shows the reduction of body weight of zebra fish by the treatment of the peptides as disclosed herein in example 3. The body weight of zebra fish was measured on day 0, 1, 3, 6, 9, 12 and 13.

FIG. 2 shows the result of the change in body weight of zebra fish. As shown in FIG. 2, the zebra fish in group 5 which was administered with AMS5 demonstrated significant reduction in body weight. After 13-week experimentation, the zebra fish administered with AMS5 reduced approximately 20 mg in average. On the contrary, the zebra fish in the rest of groups did not show the reduction in body weight.

Figure 3:
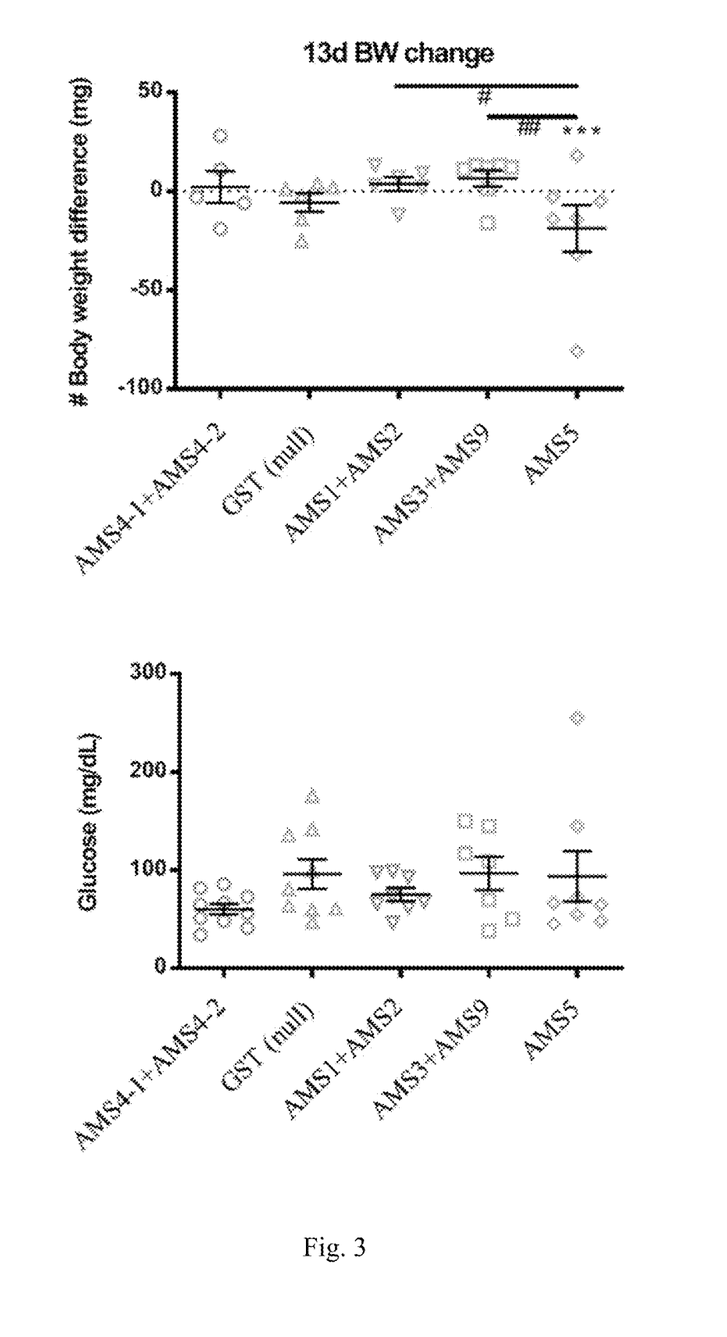
FIG. 3 shows the body weight (upper panel) and the body glucose (lower panel) of the zebra fish treated with the peptide as disclosed herein on day 13 in example 3. #: P<0.05; ##: P<0.01; *: P<0.001. (The statistics mark * refers to the comparison between the body weight on day 13 and that on day 0.)

FIG. 3 shows the distribution in body weight of zebra fish in the end of experimentation (Day 13), wherein the reduction in body weight of the zebra fish administered with AMS5 shows statistical significance. However, the glucose detected in the serum of zebra fish did not reduce (FIG. 3, lower panel).

Figure 4:
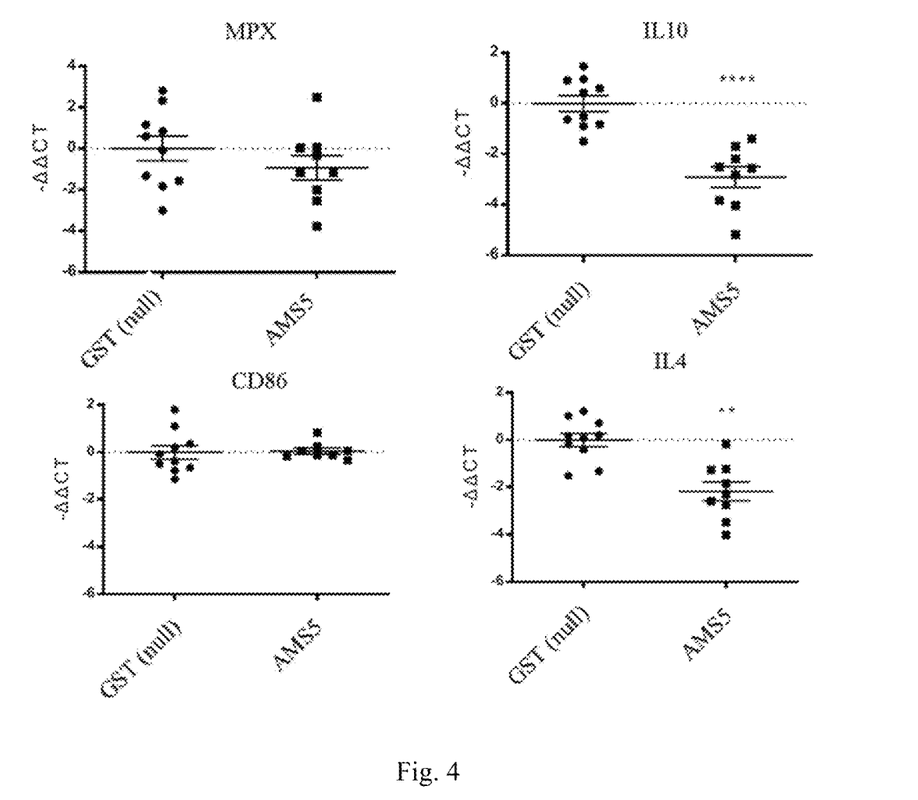
FIG. 4 shows the detection of the quantity of gene expression of MPX, IL10, CD86, ILA by qPCR for the zebra fish treated with AMS5 on day 13. Y axis (-ΔΔCT) represents the difference in the threshold cycle of amplification. : P<0.01; **: P<0.0001.

Further, the RT(reversed-transcription)-qPCR was conducted to detect the quantity of gene expression of MPX, IL10, CD86, and IL4 in the zebra fish treated with AMS5 according to the present example. The gene expression of IL10 and IL4 significantly reduced in the end of experimentation (Day 13), whereas the gene expression of MPX and CD86 did not. (FIG. 4)

It can be concluded that the peptide fragment AMS5 is capable to significantly reduce the body weight of zebra fish and the reduction in body weight is related to the reduced level of expression of IL10 and IL4, which implies that the inflammation was suppressed.

Example 4

The material and method employed in the present example is similar to that of Example 3, which is not repeated herein, except the following difference.

In the present example, five groups of zebra fish were administered with the peptides as disclosed herein:
   Group 1: AMS11-2
   Group 2: AMS11-1
   Group 3: AMS8
   Group 4: AMS5-2
   Group 5: GST (null)

Figure 5:
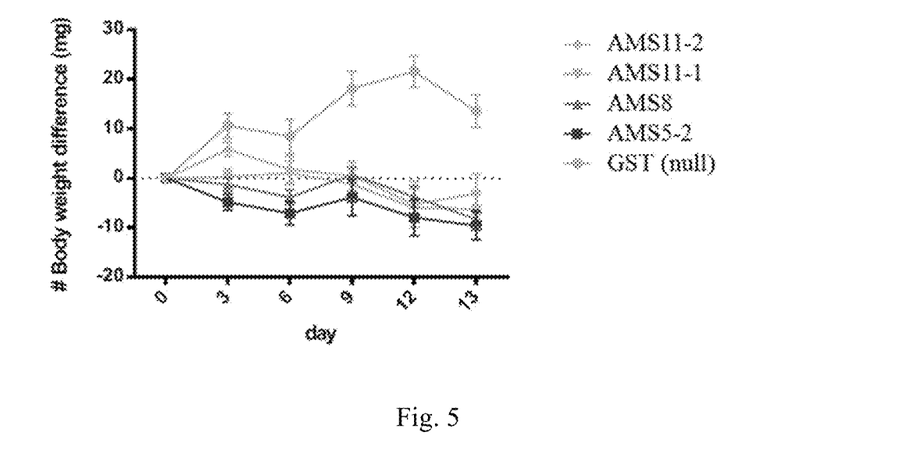
FIG. 5 shows the reduction of body weight of zebra fish by the treatment of the peptides as disclosed herein in example 4. The body weight of zebra fish was measured on day 0, 1, 3, 6, 9, 12 and 13.
Figure 6:
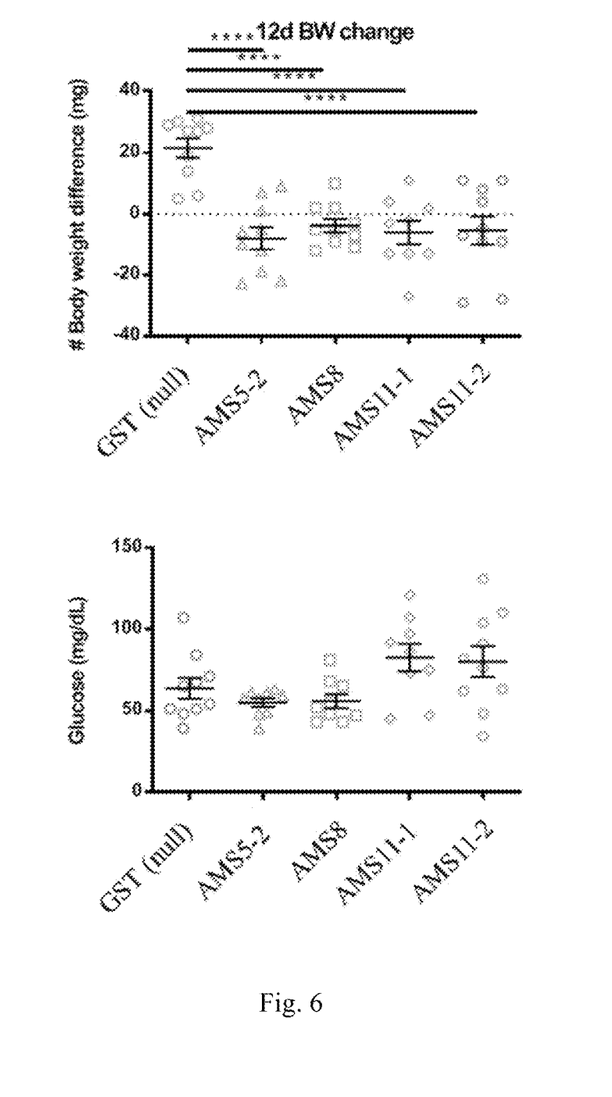
FIG. 6 shows the body weight (upper panel) and the body glucose (lower panel) of the zebra fish treated with the peptide as disclosed herein on day 12 in example 4. ****: P<0.0001.

The zebra fish in all of the groups showed significant reduction in body weight except those treated with GST (null) (FIG. 5). Furthermore, the body weight of the zebra fish was maintained in the original level as compared to the control group (GST), and the level of glucose did not change upon administration of the peptides used herein (FIG. 6).

Example 5

The material and method employed in the present example is similar to that of Example 3, which is not repeated herein, except the following difference.

In the present example, Zebra fish was bred and fed with normal diet (brine shrimp) 6 times per day and also with the peptide as disclosed herein once per day, to induce an autofat animal model.

In the present example, five groups of zebra fish were administered with the peptides as disclosed herein:
   Group 1: AMS5-2
   Group 2: Amuc_1100*
   Group 3: GST (null)

Figure 7:
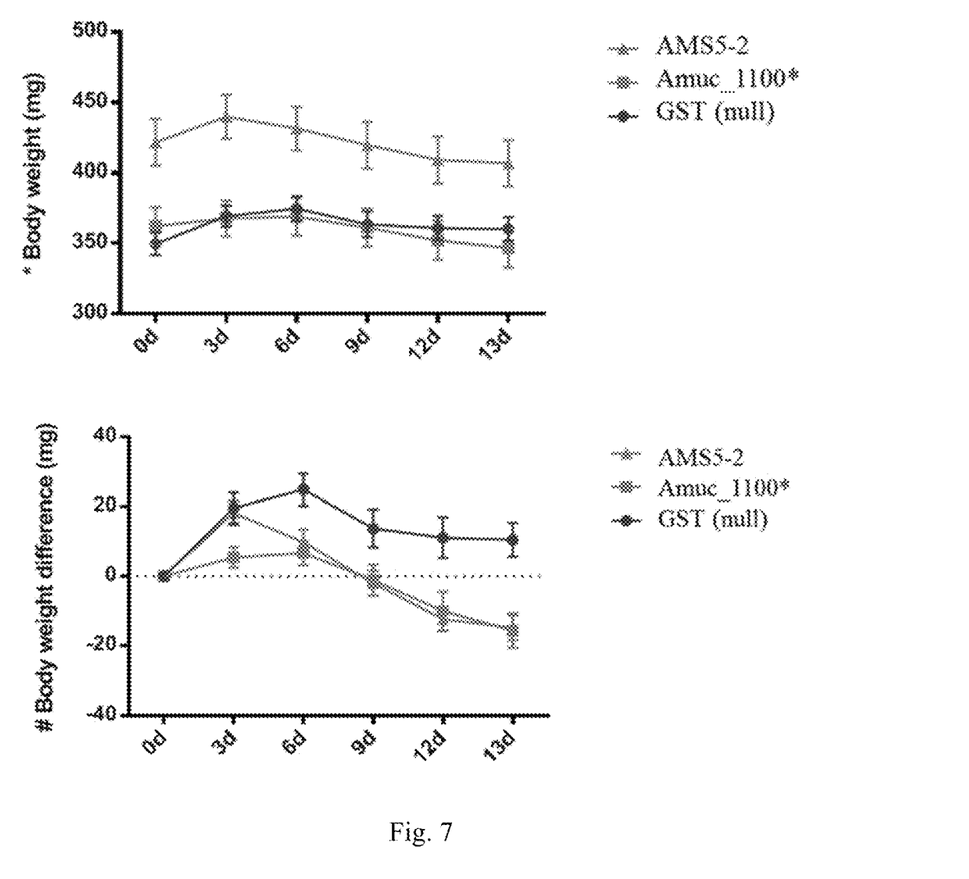
FIG. 7 shows the reduction of body weight of zebra fish by the treatment of the peptides as disclosed herein in example 5. The body weight of zebra fish was measured on day 0, 1, 3, 6, 9, 12 and 13.

The zebra fish in all of the groups showed significant reduction in body weight except those treated with GST (null) (FIG. 7).

Figure 8:
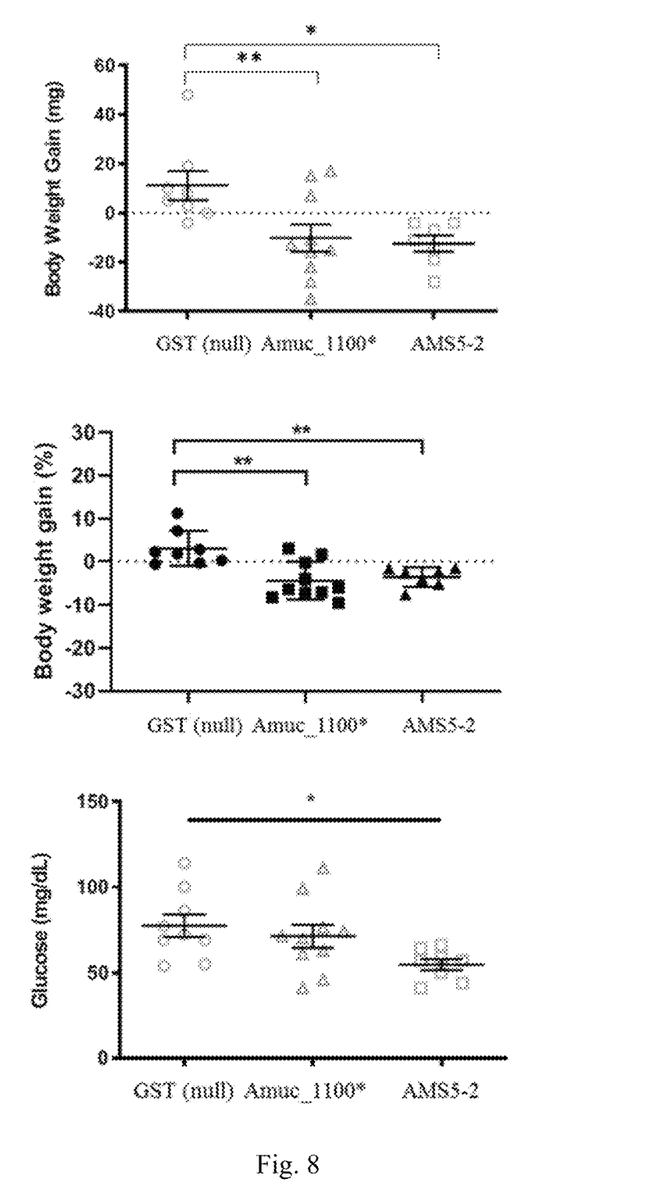
FIG. 8 shows the body weight (upper panel and middle panel) and the body glucose (lower panel) of the zebra fish treated with the peptide as disclosed herein on day 13 in example 5. *: P<0.05; **: P<0.01.

In addition, as shown in FIG. 8, in the end of experimentation (Day 13), the zebra fish treated with AMS5-2 and Amuc_1100* was further reduced as compared to the original level and the GST group. Moreover, it was observed that the level of glucose in the group treated with AMS5-2 and Amuc_1100* was reduced (lower panel in FIG. 8).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmaceutical composition comprising
    a synthetic peptide interacting with toll-like receptor 2 (TLR2) and consisting of the amino acid sequence of SEQ ID NO: 8.

2. A pharmaceutical composition for treating obesity comprising
    a synthetic peptide interacting with toll-like receptor 2 (TLR2) and consisting of the amino acid sequence of SEQ ID NO: 8.

3. A method of treating obesity in a subject in need thereof, wherein the method comprises
    administering to the subject a therapeutically effective amount of a pharmaceutical composition comprising a peptide consisting of the amino acid sequence of SEQ ID NO: 8.

4. The method as claimed in claim 3, wherein the pharmaceutical composition is administered orally or parenterally.

5. The method as claimed in claim 3, wherein the pharmaceutical composition provides an efficacy in promoting immune response.

6. The method as claimed in claim 5, wherein the pharmaceutical composition is co-administered with a vaccine and is used as an adjuvant.

7. A method of reducing intestinal carcinogen toxicity in a subject in need thereof, wherein the method comprises
    administering to the subject a therapeutically effective amount of a pharmaceutical composition comprising a peptide consisting of the amino acid sequence of SEO ID NO: 8.

8. The method as claimed in claim 7, wherein the pharmaceutical composition is administered orally or parenterally.

9. A method of treating a disease caused by intestinal epithelial barrier dysfunction in a subject in need thereof, wherein the method comprises
    administering to the subject a therapeutically effective amount of a pharmaceutical composition comprising a peptide consisting of the amino acid sequence of SEQ ID NO: 8.

10. The method as claimed in claim 9, wherein the disease caused by intestinal epithelial barrier dysfunction is inflammatory bowel disease, celiac disease, diarrhoeal diseases, type II diabetes, obesity, or non-alcoholic fatty liver disease (NAFLD).

* * * * *